US00PP18547P3

(12) United States Plant Patent
Meilland

(10) Patent No.: US PP18,547 P3
(45) Date of Patent: Mar. 4, 2008

(54) INTERMEDIATE ROSE PLANT NAMED 'MEIZULEROS'

(50) Latin Name: *Rosa hybrida*
Varietal Denomination: Meizuleros

(75) Inventor: Alain A. Meilland, Antibes (FR)

(73) Assignee: Meilland International S.A., Le Luc en Provence (FR)

( * ) Notice: Subject to any disclaimer, the term of this patent is extended or adjusted under 35 U.S.C. 154(b) by 108 days.

(21) Appl. No.: 11/431,747

(22) Filed: May 11, 2006

(65) Prior Publication Data

US 2007/0083957 P1 Apr. 12, 2007

(30) Foreign Application Priority Data

Oct. 10, 2005 (EP) ..... 2005/1868

(51) Int. Cl.
*A01H 5/00* (2006.01)

(52) U.S. Cl. ..... Plt./130

(58) Field of Classification Search ..... Plt./130, Plt./138

See application file for complete search history.

*Primary Examiner*—Annette H Para
(74) *Attorney, Agent, or Firm*—Buchanan Ingersoll & Rooney PC

(57) ABSTRACT

A new and distinct variety of rose plant of the intermediate Class is provided which abundantly forms on a substantially continuous basis attractive red-purple blossoms that are lighter in coloration on the upper surface of the petals than on the under surface. The growth habit is vigorous and erect. Attractive medium green semi-glossy foliage is formed that contrast nicely with the blossoms coloration. Tolerance to diseases is good particularly with respect to Oidium. The new variety forces well under greenhouse growing conditions and is well suited for cut flower production under such conditions.

1 Drawing Sheet

Figures 1, 2, 3, 4, 5, 6, 7, 8, 9, 10, 11, 12, 13, 14, 15:
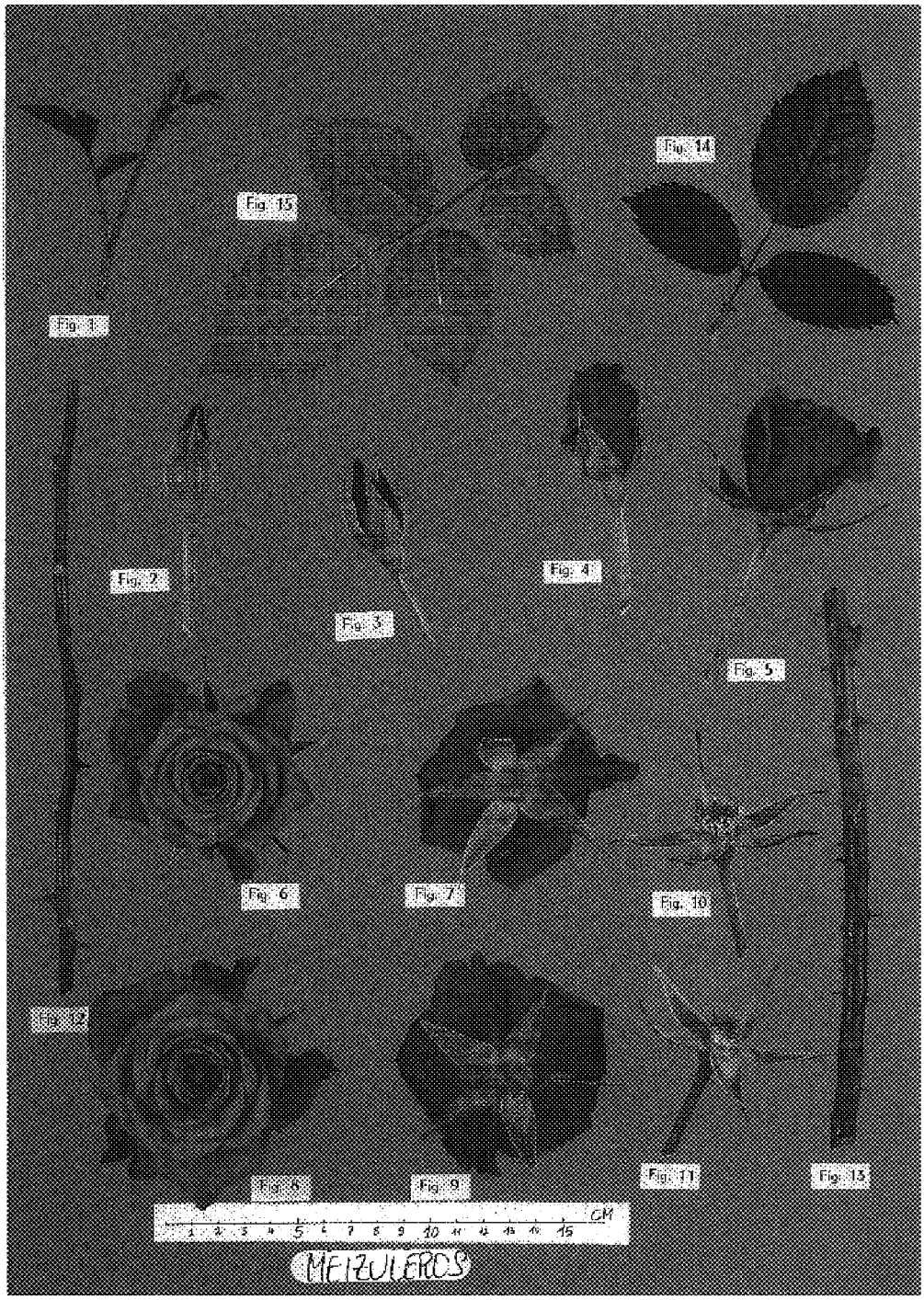

Botanical/commercial classification: *Rosa hybrida*/Intermediate Rose Plant.
Varietal denomination: cv. 'Meizuleros'.

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Olijplam' variety (non-patented in the United States). The male parent is the product of the cross of the 'Korikis' variety (non-patented in the United States) and the 'Olytel' variety (U.S. Plant Pat. No. 8,862). The parentage of the new variety can be summarized as follows:

'Olijplam'×('Korikis'×'Olytel'.

The seeds resulting from the above pollination were sown and small plants were obtained which were physically and biologically different from each other. Selective study resulted in the identification of a single plant of the new variety.

It was found that the intermediate rose plant of the present invention possesses the following combination of characteristics:

(a) exhibits a vigorous and erect growth habit, (b) forms in abundance on a substantially continuous basis attractive red-purple blossoms that are lighter in coloration on the upper surface of the petals than on the under surface, (c) forms attractive medium green semi-glossy foliage that contrasts well with the blossom coloration, and (d) is particularly well suited for cut flower production under greenhouse growing conditions.

The tolerance to diseases is good particularly with respect to Oidium.

The new variety of the present invention can be readily distinguished from its parental varieties. More specifically, the 'Olijplam' variety displays considerably more thorns, the blossoms of the 'Korikis' variety are a lighter pink, and the blossoms of the 'Olytel' variety are cream margined with pink in coloration.

The new variety performs well under greenhouse growing conditions while producing cut flowers.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meizuleros' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa indica major* understock and growing outdoors at Le Cannet des Maures, Var, France. Dimensions in centimeters are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface; and FIG. 15 — illustrates a specimen of a leaf with five leaflets — plan view — under surface.

DETAILED DESCRIPTION

The chart used in the identification of the colors is that of the Royal Horticultural Society (R.H.S. Colour Chart). The description is based on the observation of two year-old plants during September while budded on *Rosa indica major* understock and growing under greenhouse conditions at Le Cannet des Maures, Var, France.

Class: Intermediate.

Plant:

*Height.*—When pruned to a height of 0.85 cm, floral stems having lengths of approximately 50 to 70 cm commonly are produced.

*Habit.*—Erect.

Branches:

*Color.*—Young stems: near Green Group 138A. Adult wood: near Green Group 137A.

*Thorns.*—Configuration: rather straight, very longish pointed, curved downwards on the upper surface, and very concave on the under surface. Size: approximately 0.8 cm in length on average with an ovate base on young stems, and approximately 1 cm in length on average with an ovate base on adult stems. Quantity: approximately 8 on average over a young stem length of 10 cm, and approximately 4 on average over an adult stem length of 10 cm. Color: near Yellow-Green Group 144B on young stems, and near Greyed-Orange Group 165A and 165B on adult stems.

*Prickles.*—Size: approximately 0.4 cm in length on average with an ovate base. Quantity: approximately 4 on average over a stem length of 10 cm Leaves:

*Stipules.*—Smooth, adnate, pectinate, narrow. Approximately 1.1 cm in length on average, approximately 0.1 cm in width on average, and near Yellow-Green Group 146B on the upper and under surfaces.

*Petioles.*—Upper surface: near Green-Group 137B. Under surface: near Green Group 137C. Length: approximately 2 cm on average.

*Rachis.*—Upper surface: near Green Group 137B. Under surface: near Green Group 137C.

*Leaflets.*—Number: 3, 5 (most often), and 7. Shape: elliptic with a pointed tip and a rounded base. Serration: single and fine (as illustrated). Texture: firm, and semi-glossy. General appearance: dense and medium green. Size: terminal leaflets commonly measure approximately 6 cm in length, and approximately 4 cm in width. Color (young foliage): upper surface: near Yellow-Green Group 147A suffused with Greyed-Red Group 178A. Under surface: near Yellow-Green Group 147B suffused with Greyed-Red Group 178A. Color (adult foliage): upper surface: near Yellow-Green Group 147A. Under surface: near Yellow Green Group 147B.

Inflorescence:

*Number of flowers.*—Commonly one flower per stem.

*Peduncle.*—Glandular, near Yellow-Green Group 144A in coloration, approximately 3.3 cm in length on average, and approximately 0.4 cm in diameter on average.

*Sepals.*—Upper surface: tomentose, and near Green Group 138B in coloration. Under surface: glandular, and near Yellow-Green Group 144A in coloration. Length: approximately 3.2 cm on average. Width: approximately 0.9 cm on average. Shape: longish pointed and narrow. Extensions: commonly three sepals possess very weak extensions and two sepals commonly possess no extensions.

*Buds.*—Shape: conical. Size: medium. Length: approximately 3.2 cm on average. Width: approximately 2 cm on average. Color as the calyx breaks: upper surface: near Red-Purple Group 63B and 63C and amply suffused with Red-Purple Group 63A and margined with Red Group 53B. Under surface: near Red Group 53A and 53B.

*Flower.*—Shape: cup-shaped. Diameter: approximately 7 cm on average when open. Color (in the course of opening): upper surface: near Red-Purple Group 63C and amply suffused with Red-Purple Group 63B and margined with Red-Purple Group 63A. Under surface: Near Red Group 53B and 53C. Color (when open): Upper surface: Near Red-Purple Group 65C and amply suffused with Red-Purple Group 63B and 63C. Under surface: near Red Group 53D and amply suffused with Red-Purple Group 63A. Basal color spot: absent on both surfaces. Color stability: slight lightening in coloration on the upper surface at the end of blooming. Lasting quality: very long and commonly approximately 20 to 21 days on average on the plant and approximately 15 to 18 days on average when out and placed in a vase. Petal number: commonly approximately 40 on average under normal growing conditions. Petal arrangement: imbricated. Petaloids: none observed. Petal shape: obtuse base, rounded tip, approximately 4.1 cm in length on average, and approximately 4 cm in width on average. Petal texture: consistent. Petal drop: good, the petals commonly detach cleanly before drying. Fragrance: none. Stamen number approximately 104 on average. Anthers: near Yellow-Orange Group 21C in coloration, approximately 3 mm in size, and regularly arranged around the styles. Filaments: near Red Group 56D in coloration, and approximately 0.7 cm in length. Pistils: approximately 171 on average. Stigmas: near Red Group 47B in coloration, and approximately 0.1 cm in size on average. Styles: near Yellow-Orange Group 14C in coloration, and the length is approximately 0.6 cm on average. Hips: none observed to date under greenhouse growing conditions.

Development:

*Vegetation.*—Very vigorous.

*Blooming.*—Medium season, very abundant and substantially continuous.

*Tolerance to diseases.*—Good especially with respect to Oidium.

*Aptitude to forcing.*—Excellent.

I claim:

1. A new and distinct intermediate rose plant which exhibits the following combination of characteristics:

(a) a vigorous and erect growth habit, (b) forms in abundance on a substantially continuous basis attractive red-purple blossoms that are lighter in coloration on the upper surface of the petals than on the under surface, (c) forms attractive medium green semi-glossy foliage that contrasts well with the blossom coloration, and (d) is particularly well suited for cut flower production under greenhouse growing conditions;

substantially as illustrated and described.

* * * * *

CM
MFIZULEROS